US008333469B2

(12) United States Patent
Filipovich et al.

(10) Patent No.: US 8,333,469 B2
(45) Date of Patent: Dec. 18, 2012

(54) METHOD AND SYSTEM FOR PROVIDING FINANCIAL DATA FOR OPTICAL LABS SHARING LENS CALCULATION SOFTWARE

(75) Inventors: Mike Filipovich, Ottertail, MN (US);
Konstantinos Voyiatzis, Dallas, TX (US); Steve Morris, Flower Mound, TX (US); John Forner, St. Cloud, MN (US); Paul Nordin, Wilmar, MN (US)

(73) Assignee: Essilor International (Compagnie Generale d'Optique), Charenton-le-Pont (FR)

( * ) Notice: Subject to any disclaimer, the term of this patent is extended or adjusted under 35 U.S.C. 154(b) by 761 days.

(21) Appl. No.: 12/112,518

(22) Filed: Apr. 30, 2008

(65) Prior Publication Data

US 2009/0276238 A1  Nov. 5, 2009

(51) Int. Cl.
*G02C 7/02* (2006.01)
(52) U.S. Cl. ........................................ 351/159.01; 451/5
(58) Field of Classification Search .............. 705/2, 27; 451/5; 700/198; 62/141; 351/178, 177
See application file for complete search history.

(56) References Cited

U.S. PATENT DOCUMENTS

| | | | |
|---|---|---|---|
| 4,908,997 A * | 3/1990 | Field et al. .................. 451/5 |
| 5,485,399 A | 1/1996 | Saigo et al. | |
| 6,381,012 B1 | 4/2002 | Yancy | |
| 6,890,241 B2 | 5/2005 | Kozakai et al. | |
| 7,044,601 B2 | 5/2006 | Wang et al. | |
| 7,139,636 B2 | 11/2006 | Foreman et al. | |
| 7,188,082 B2 * | 3/2007 | Keane et al. ................ 705/27 |
| 2004/0032565 A1 * | 2/2004 | Yamakaji et al. .......... 351/177 |

* cited by examiner

*Primary Examiner* — Valerie Lubin
(74) *Attorney, Agent, or Firm* — Keusey & Associates, P.C.

(57) ABSTRACT

A method and system for allowing multiple geographically distributed optical labs to share global resources over a telecommunications network. Each optical lab is set up as a client account on the server with privileges to access the global recourses. Each lab has its own equipment set, the settings and configuration of which, are recorded in one of the client account databases. Other proprietary databases contain price lists, financial information and patient data. The lens calculation software encounters a sequential stream of job requests from different client accounts. The corresponding proprietary account data, allows uniform pricing rules to be applied to lens processing jobs. As jobs are completed, each lab receives an individual packet of printable job ticket data, printable invoice data, electronic interface files for the lens generating equipment, and an extract file for importing into the labs accounting software.

26 Claims, 5 Drawing Sheets

METHOD AND SYSTEM FOR PROVIDING FINANCIAL DATA FOR OPTICAL LABS SHARING LENS CALCULATION SOFTWARE

BACKGROUND OF THE INVENTION

1. Technical Field

The present invention relates generally to a method and system for providing job invoicing information for customers of optical labs within a shared software environment.

2. Description of Prior Art

Some ophthalmic lenses can be molded to a final power, for example single vision (SV) lenses, having a power of +1.00 diopters. Other lenses are only molded to an intermediate state, for example, semi-finished lenses. These intermediate lenses must undergo additional processing steps to achieve the final power or to create custom optical features. Almost all lenses must be edged to shape the periphery of the lens to match the frame.

Various types of computer networks and software may be utilized to communicate lens type and prescription data, to place orders or to calculate how a lens will be generated. U.S. Pat. No. 6,381,012 utilizes a lens tracing pen and template to determine and transmit optical lens sizing and prescription data. The system may be used to assist doctors in specifying a prescription to be used with a given lens configuration. As shown in FIG. 1 of the patent, a lens marker, lens blocker or lens edger 28 is connected to the server for centralized processing of lenses.

U.S. Pat. No. 5,485,399 describes a client computer which communicates lens, prescription and frame data over a network. The server calculates desired lens shape including a bevel, and then communicates to the client computer, for display to the user, whether the bevel is compatible with the selected frame.

U.S. Pat. No. 7,139,636 describes a method for making a cast lens where a prescription is communicated to a server containing lens processing software. The software identifies two mold members to cast the lens. The client computer also receives a job ticket which can be printed to accompany the molds and lens during manufacturing.

U.S. Pat. No. 7,044,601 transmits prescription data over a network to a server that utilizes a proprietary technique to calculate a method for grinding a lens to provide a progressive optical feature. Other large-scale software like Optifacts® can be used in the instant invention and works similarly to calculate surface grinding parameters for a particular prescription.

U.S. Pat. No. 6,890,241 describes a network system where quality control can be managed by a single server overseeing client manufacturing cells. The system is for processing large volumes of the same glass lenses in a factory setting. Operators frequently measure finished lenses and upload the data to the server. The server utilizes the measurement statistics over time to fine tune the machine settings in a feedback loop.

In the processing of plastic lenses based on a customers prescription, each lens that needs to be processed is different from the next. Accordingly, each lens or lens pair has its own processing cost based on complexity. In addition, when multiple clients share large-scale lens management software, the technical and financial data of each client must be maintained in confidence.

What is needed is a method and system for allowing geographically remote clients to share large-scale resources in a secure manner. Additionally, financial account information would allow individual pricing data to be transmitted to each client along with technical data, like job tickets and lens calculation files.

SUMMARY OF THE INVENTION

Accordingly, it is an object of the present invention to allow a number of small labs to share large scale computer resources to benefit from the economies of scale.

It is a further object to provide optical lab management software that can globally and sequentially perform lens calculations for many different lab clients.

It is another object to provide a common lens database with comprehensive and updated data on all lens SKUs for the client labs.

It is a further object to have each client lab account maintain proprietary technical and financial data relating to its operations.

It is another object to have the proprietary account data interact with the global resources to provide individual job and pricing information corresponding to each prescription lens order.

These and other related objects according to the invention are achieved by a method of providing job invoicing information for customers of optical labs within a shared software pay-per-use environment. The method includes configuring a client account for each optical lab which comprises one client out of a plurality of clients communicating with a lab management server over a geographically distributed telecommunications link. Each client account includes proprietary financial resources and access to global technical resources comprising a global lens database and a lens calculation program shared by all labs, and proprietary data records for each optical lab which includes an equipment configuration database containing machine parameters, and price lists and financial spreadsheets.

Once configuration is complete, a job request is processed for an individual prescription via an order entry facility on the client with the details of the job being transmitted to the server. The job request is run on the lab management serving utilizing global resources with the proprietary parameters of the requesting lab and completed job data is returned with individual pricing. The configuration allows proprietary lab parameters to be maintained persistent across multiple individual Rx orders for the respective lab's customers.

In a commercial operating environment, the various optical lab clients alternately submit new job requests. Each submission prompts an instance of the job request processing step and the job request running step. Collectively, the processing and running steps are repeated, each time for a different optical lab client and for a sequence of unique lens orders, wherein each optical lab client uses its same proprietary lab parameters for all jobs.

The global lens database includes data on more than 400,000 individual lens SKUs, and the proprietary price lists categorize lenses by a combination of material and lens type. Each category includes a series of financial spreadsheets based on another lens feature selected from the group consisting of sphere, power, lenticulars, prescription, over power, add power, add type, add size, prism, tints, polarization, lens colors, lens coatings and compatible combinations thereof.

The configuring step includes calibrating the lab's equipment set. The lab equipment may include a generator, a blocker, and edger. The equipment configuration database is based on equipment type. The machine parameters are based on equipment calibration. The job processing step includes providing certain data selected from lens type and material data, frame trace data and a lens package bar code. The returned completed job data may include a printable job ticket file, a printable invoice file and an extract file containing the invoice financials. The format of the extract file is determined by the proprietary data records. The format is suited for exporting the extract file to the particular labs accounting software.

Another aspect of the invention is a software product adapted to be stored in a memory of a client processor unit, or in removable memory medium adapted to cooperate with at least one of a reader of the processor unit and a remote source via a telecommunications network. The client software includes instructions for implementing at least one step of the method outlined above. A further aspect is a software product including lab management software adapted to be stored in a memory of a server processor unit, or in removable memory medium adapted to cooperate with at least one of a reader of the processor unit and a remote source via a telecommunications network. The lab management software includes instructions for implementing at least one step of the method outlined above.

In an alternate embodiment there is provided a system for processing a plurality of unique ophthalmic lens job requests including invoicing information for patients of optical labs within a shared software pay-per-use environment. The system includes a lab comprising one client out of a plurality of clients. The client, or client computer, is equipped with an order entry facility for collecting individual lens data including prescription data and for initiating a job request to the server. A telecommunications link operatively connects the clients to the server. The server comprises a lab management server having global services including a lens database to identify the lens properties/type from the job request, proprietary technical and financial data records for each client lab, and global lens calculation software that is customized for each lab by the proprietary data. Each client facility includes lens generating equipment having machine parameters that are stored within the proprietary data for interacting with the global lens calculation software to provide unique lens calculations to be generated according to a corresponding job ticket. The proprietary data allows a plurality of client labs to share global resources and deliver a continuous series of individual lenses and provide corresponding individual pricing for electronic and paper invoicing.

The system includes three operating states including: a calibration mode for recording settings of the lens generating equipment within the proprietary technical data records; a normal operating mode where unique lens jobs are sequentially processed; and a financial mode for delivering individual pricing and individual invoicing and individual accounts receivable electronic extract files to the lab. The system initially operates in calibration mode to set up a new lab as an additional client account on the server. After initial operation of the calibration mode, the system interacts with existing client accounts to alternately operate between normal operating mode and financial mode to produce a continuous stream of unique job tickets, lenses, invoices, and accounting extract files all corresponding to a particular Rx. Once the system exits calibration mode, the generating equipment is isolated from providing quality control feedback to the server. Operation within the calibration mode comprises recording equipment settings for a lens generator, blocker and edger, wherein the equipment settings are based on equipment type and equipment calibration.

The order entry facility collects additional lens data selected from lens type, lens material, frame trace data, scanned lens package bar code data, and combinations thereof. Another aspect of the system is a software product adapted to be stored in a memory of a client processor unit, or in removable memory medium adapted to cooperate with at least one of a reader of the processor unit and a remote source via a telecommunications network. The client software includes instructions for interacting with at least one element of the system as described above. A further aspect is a software product including lab management software adapted to be stored in a memory of a server processor unit, or in removable memory medium adapted to cooperate with at least one of a reader of the processor unit and a remote source via a telecommunications network. The server software instructions for interacting with at least one element of the system as described above.

BRIEF DESCRIPTION OF THE DRAWINGS

The advantages, nature and various additional features of the invention will appear more fully upon consideration of the illustrative embodiments now to be described in detail in connection with the accompanying drawings. In the drawings wherein like reference numerals denote similar steps and components throughout the views.

It should be understood that the drawings are for purposes of illustrating the concepts of the invention and are not necessarily the only possible configuration for illustrating the invention.

DETAILED DESCRIPTION OF PREFERRED EMBODIMENTS

Figure 1:
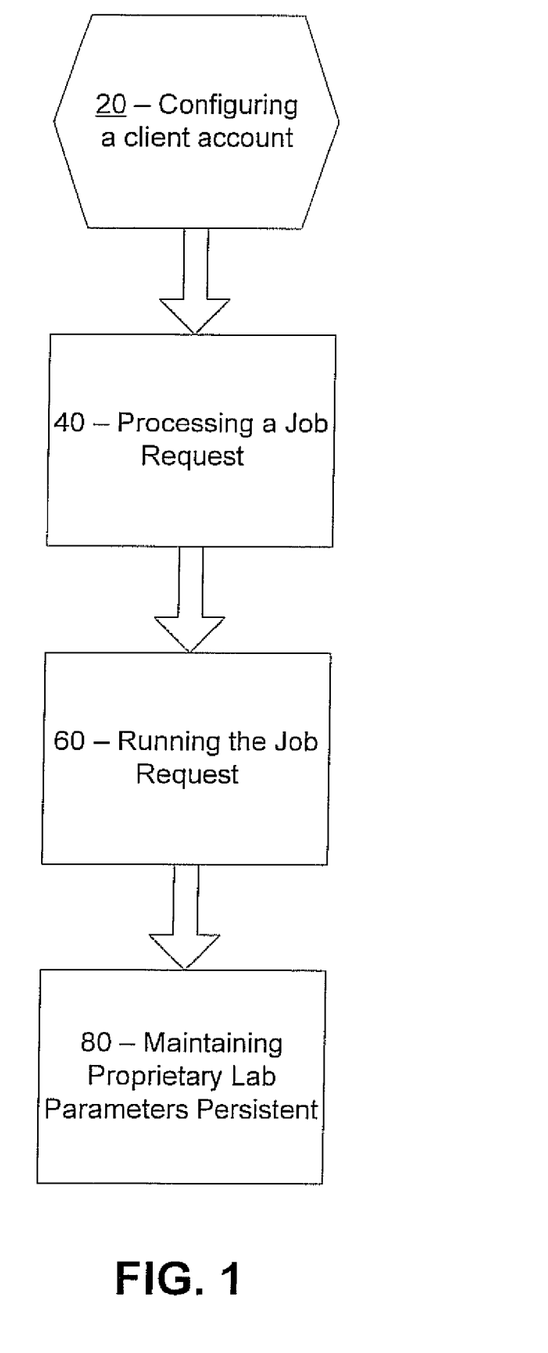
FIG. 1 is a block flow diagram of a method by which a client lab can obtain financial data with a prescription lens job request according to an aspect of the present invention.

Referring now in detail to the figures, FIGS. 1 through 4 are block flow diagrams illustrating various steps which comprise the method according to the invention. The rectangular blocks represent customary "process" steps. The six-sided blocks represent "preparation" steps. The trapezoids of steps 42 and 44 represent "manual input" steps. FIG. 1 is a general overview of the key steps to be performed in the execution of the method. The first three steps are then explained in further detail in FIGS. 2, 3 and 4, respectively. In other words, the latter flow charts show sub-steps of the main method. It should be understood, that some of the sub-steps represent optional features of the invention, and that a fewer number of sub-steps may be contemplated within the scope of the invention.

In FIG. 1, step 20 comprises Configuring a client account. It is expected that dozens or more clients will be part of the system. The clients are likely to be geographically distributed, and many will be independent business entities have no legal or business tie between them. To bring a new client into the system, a preparatory configuration step 20 is executed.

Greater details concerning the configuration step will be provided below in connection with FIG. 2.

After the client is configured and set up, they can process a job request in step 40. Generally this involves interacting with a patient that wishes to order prescription (Rx) lenses. The various aspects of the processing step will be discussed in greater detail in connection with FIG. 3 below. On the server side, the requested job is run in step 60. Jobs will be requested randomly from the various clients. Those jobs will be queued and run sequentially, taking advantage of the access to the large scale software. The running step will be discussed in greater detail with respect to FIG. 4 below.

In step 80, we maintain proprietary lab parameters persistent across multiple Rx orders, for each lab. However, each job sequenced into the large scale lens management software will have a different set of proprietary lab parameters, depending on which client requested that job. In prior systems, one large lab would locally run its own copy or version of the lab management software. Proprietary lab parameters would not need to be maintained because the software is preparing interface files for the same set of equipment each and every time.

Figure 2:
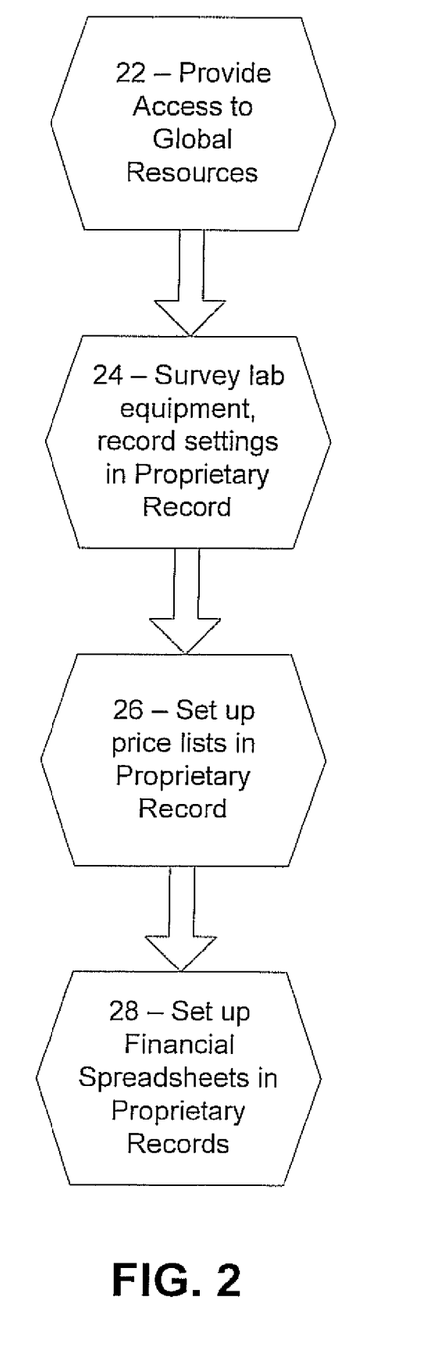
FIG. 2 is a block flow diagram detailing the configuration step.
Figure 5:
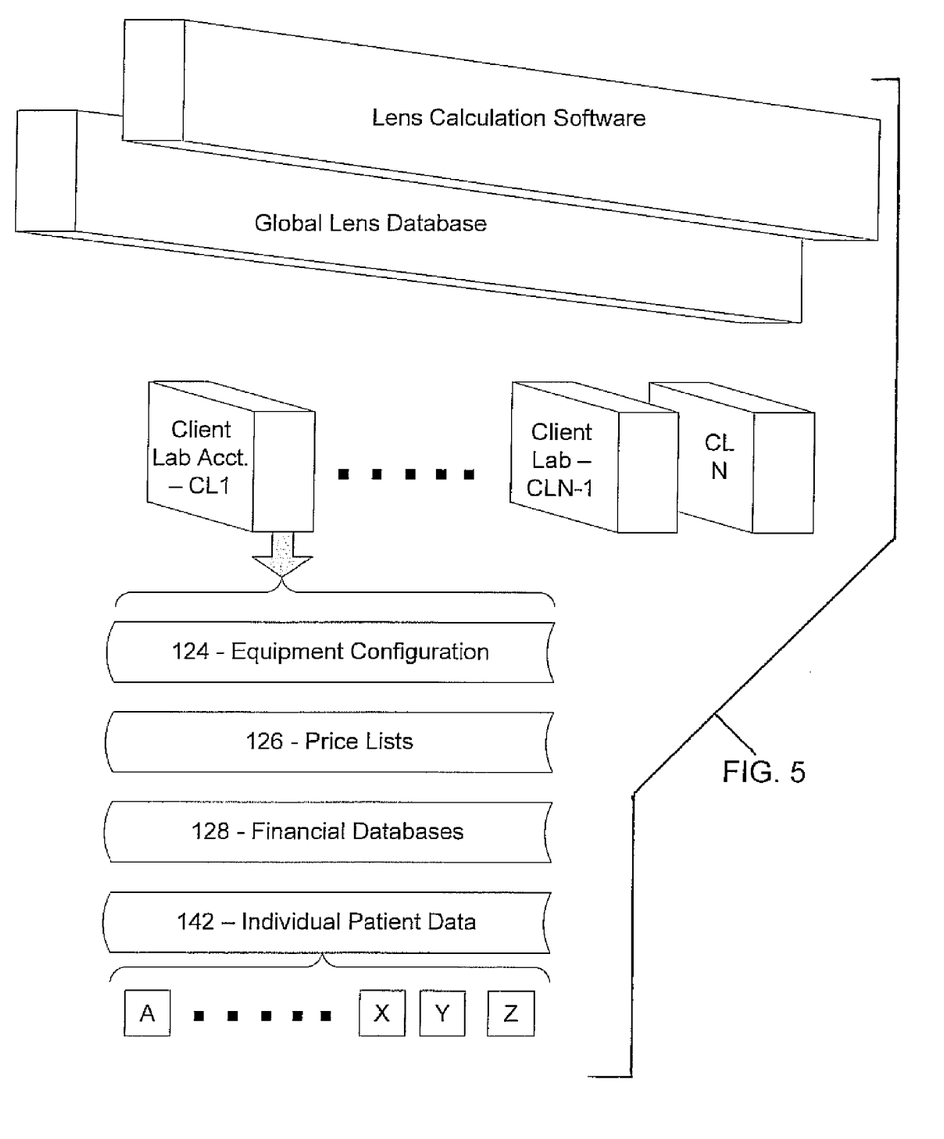
FIG. 5 is a schematic drawing of the system components including proprietary databases according to an aspect of the invention.

Referring now to FIGS. 2 and 5, there is a "preparation" step of configuring a new client account from step 20. Steps 22-28 are part of the more general step 20. Each client account corresponds to an optical lab. The client lab accounts are numbered from CL1, CL2, CL3 through CLN-2, CLN-1, CLN. FIG. 5 shows the new client lab account $CL_1$ operatively positioned adjacent the global lens calculation software and the global lens database. In this manner, the client account has access to the global resources per step 22. All other client accounts are similarly situated.

At installation each client program is configured with a unique Lab ID, Account Number and Password. Once configured and connected to the Internet the client program will communicate with the server system and update the client's program and lens database information to the most current release.

On the lab side, at installation, the client program is also configured so it can handle interface communications with each generator, edger, blocker and tracer in the lab. Serial cables are connected between the ports on the supplied RS-232 hub and each machine. A specific client system background program for each machine is started that handles communications between the client system and each specific machine. Per step 24, we conduct a survey of the lab equipment, and record the settings in the first proprietary record 124, called Equipment Configuration.

At installation of the pricing/invoicing features, the user must configure and maintain a number of pricing lists 126 and spreadsheets 128. These lists and spreadsheets are uploaded to the server and stored in each lab's unique calculations database, in steps 26 and 28. The server uses these lists and spreadsheets to calculate each job's invoice total price and subtotals by pricing category.

Figures 3, 4:
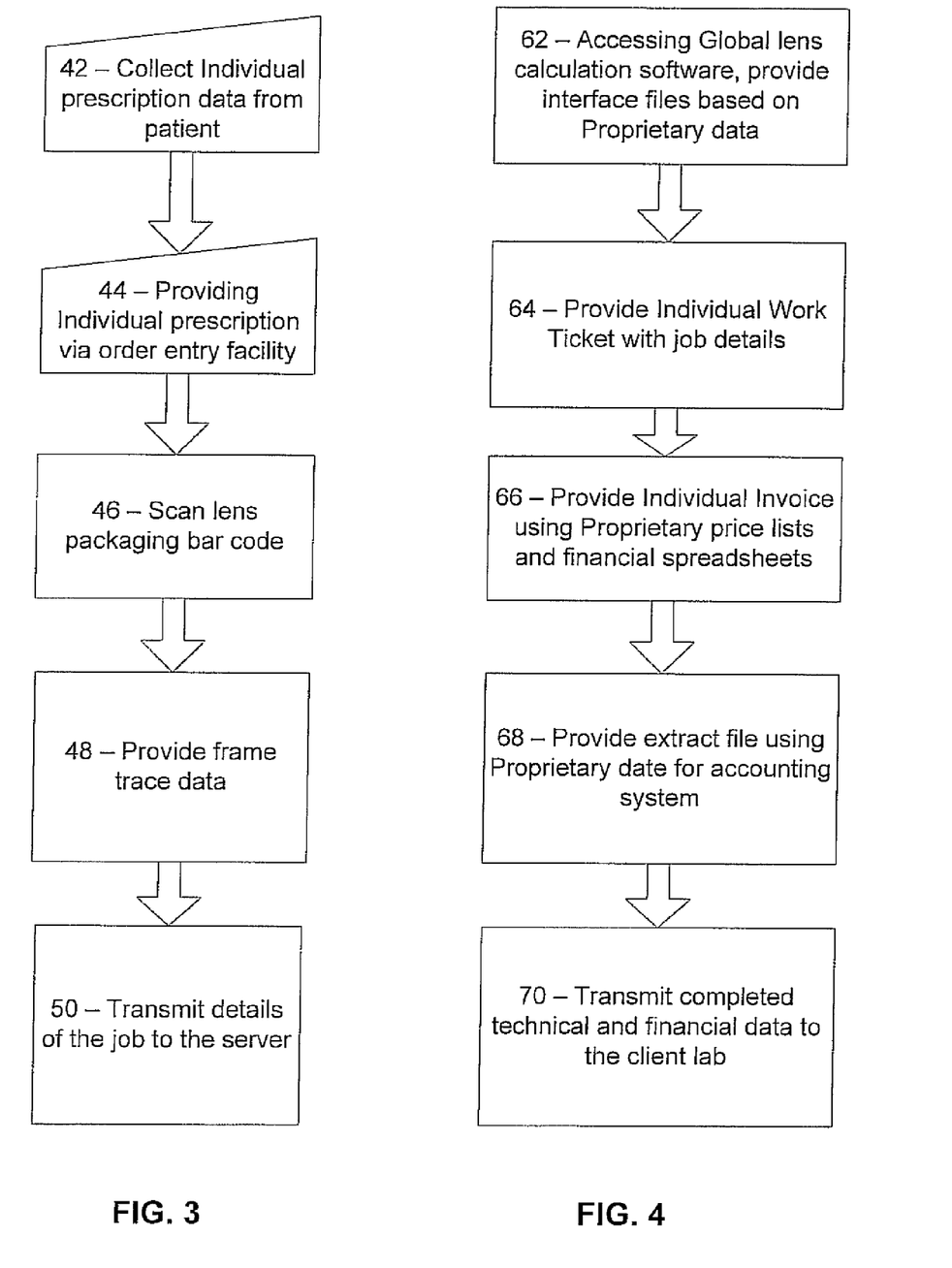
FIG. 3 is a block flow diagram detailing the job processing step.
FIG. 4 is a block flow diagram detailing step involved in running a job.
Figure 6:
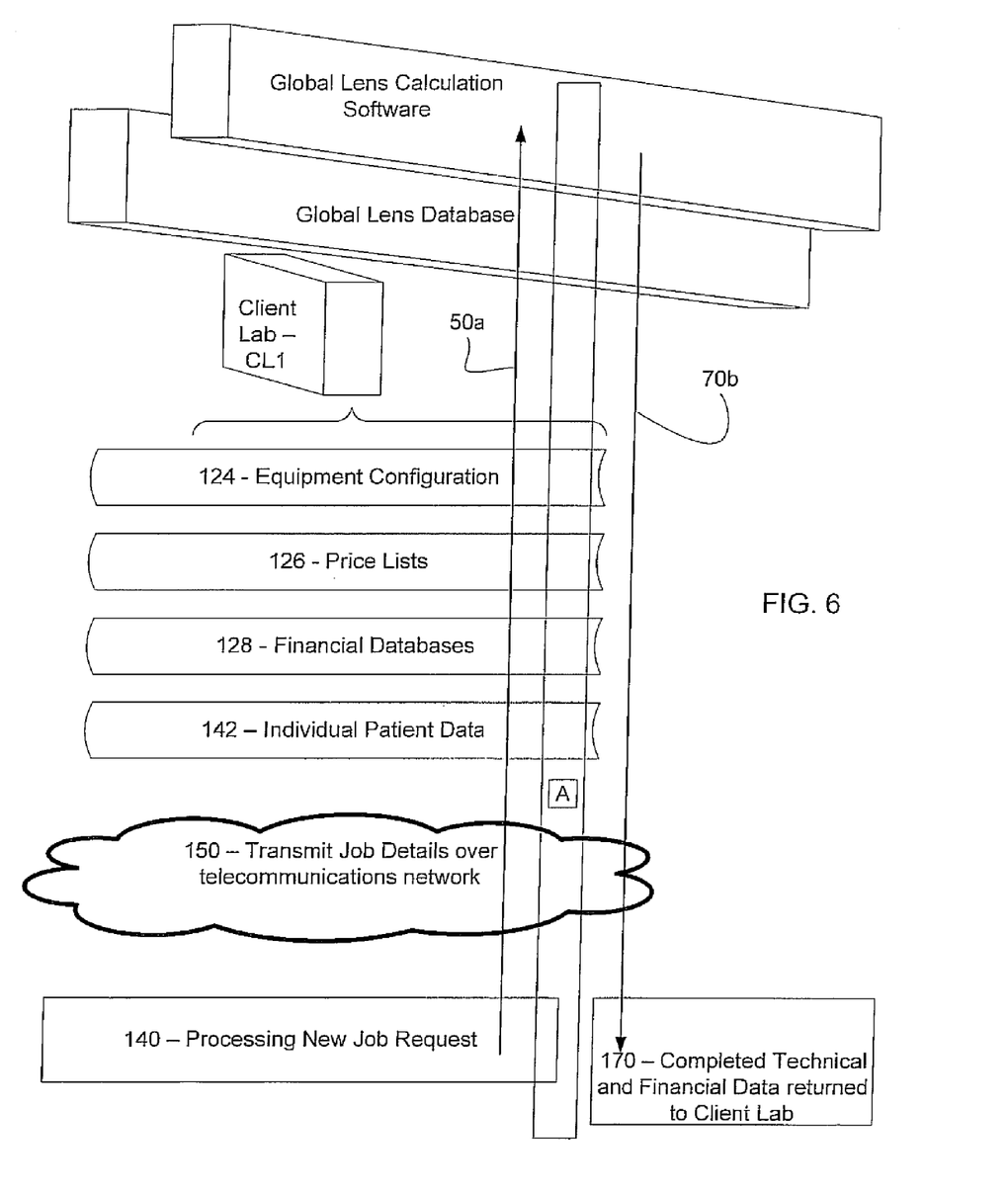
FIG. 6 is a schematic drawing showing the job request path through the various components of the system.

As can be seen in FIGS. 3 and 6, a job request is processed per step 40. In step 42 prescription data and other personal information, like contact information, is collected from the patient. Job files are created for each order on the Client system by the user entering Rx information into the program using the order entry facility 44. The user also selects the lens blanks to use for each job from a popup dialog window. A final popup dialog allows the user to select additional pricing options and/or processing steps to perform to the job. The job is then saved to a file. The client PC may be equipped with a bar code scanner for reading the bar code from the lens packaging 46. Another option is to provide frame trace data 48 via an appropriate input device. Per step 50, the detail of the job are transmitted to the server. FIG. 6 shows a telecommunications network 150 which allows all of the clients to connect into the lens management server. The arrow 50$a$ represents the transmission of individual job data from the processing module 140 to the patient database 142; the assignment of proprietary information from databases 124, 126, 128 to that job; and access to the global resources.

As can be seen in FIGS. 5 and 6, the received data is stored in individual patient data files within database 142. The individual patients are identified as patients A, B, C through patients X, Y, Z. Each client lab has its own set of databases 124, 126, 128 and 142. As can be seen in FIGS. 1, 4 and 6, the job request is processed in 40 and 140 and transmitted via 150 to the client lab $CL_1$ account at the server. Although the proprietary technical and financial data is fixed and applied in a uniform manner to the global resources, a series of unique outputs and products are obtained. For client lab 1, this can be represented by the set, $CL_1A, CL_1B, CL_1C \ldots CL_1X, CL_1Y, CL_1Z$. All of the sets can be represented in a matrix with the following exemplary form.

$CL_1A, CL_1B, CL_1C \ldots CL_1X, CL_1Y, CL_1Z$
. . .
. . .
. . .
$CL_{N-1}A, CL_{N-1}B, CL_{N-1}C \ldots CL_{N-1}X, CL_{N-1}Y, CL_{N-1}Z$
$CL_NA, CL_NB, CL_NC \ldots CL_NX, CL_NY, CL_NZ$ Previously, use of large scale lab management software in-house, did not provide for a variety of independent users, represented by the N number of rows above. In other instances, where large numbers of the same lenses were being processed, there was not a variety of unique product deliverables, represented by the A to Z number of columns above. In both cases information was shared or public, between the clients. The system according the invention is scalable both vertically by adding rows, or horizontally by adding patients. The prior art does not contemplate the uniform application of multiple sets of proprietary technical and financial rules represented by N, to global resources on a patient by patient basis represented by Z for each client lab, to obtain N*Z individual results.

For the technical data, a combination of the individual Rx, the proprietary information in databases 124 and access 62 to the global lens calculation software and the global lens database, allows the unique job to be processed. Interface files that control the operations of the generator, blocker and edger machines are created and returned to the client 70, 170. The user can then go to any of these machines and request the interface file. The client program will process the request, read the interface file and return the appropriate data response to each machine. If the file does not exist the client program will return a "job not found" message to the machine.

Each lab has its own set of lens calculation programs. They watch for existence of a new job file. When a job file is found it is read. The calculations program will then produce the set of work ticket, invoice and interface files that will be returned to the client system.

For the financial data, information from databases 126 and 128 will create an individual invoice in step 66. An extract file may also be created in step 68, which can be exported by the client lab directly into their accounting program. All needed data is transmitted back to the client lab via step 70. This return path is illustrated by arrow 70$b$, terminating with the completed technical and financial data at the client location 170. Transmissions are facilitated by an internet communications software package, which handles the processing of all incoming client program requests and file transfers. The program validates each lab's request. If the lab is sending a job for processing the communications program will store the job in the appropriate, unique, calculations folder for that lab. After a job has been processed the Internet communications program will automatically return the calculated work ticket, invoice, financial extract file and machine interface files to the client system Existing systems do not contemplate a lab management server with shared access to global resources. For example, in large labs, the lab management software is in-house, is not shared, and has a fixed set of equipment that it interfaces with. Accordingly, the in-house [local] software runs all jobs for the same one set of equipment. There are no propriety or confidential aspects because all of the components are under one roof. In the method and system according to the invention, the jobs are randomly received from different Client Lab accounts. The [global] software resources are shareable, only because the client databases are proprietary and the information contained therein is maintained confidentially from each other. Each completed machine interface file is for a geographically remote lab.

Other optical labs mass produce large batches of the same lens. A machine interface file need only be generated one time, and then used over and over again. Since all jobs are the same, there is no need for individual items, like job tickets, invoicing and accounting extract files. The mass production is in effect the opposite, of producing a continuous series of individual lenses. Some of these systems collect quality control data about the machine's precision. This data is used to update software setting in a feedback loop.

There are multiple database systems maintained on the server, categorized as global, proprietary and individual. A common, shared, global database holds all lens blank information. An extract of the lens database is done whenever new lenses are added to the database or old product is changed or deleted. This extract is sent to all client systems as a lens database update. The extracted information is presented to the user when they choose a lens to use for each job.

Each lab configured on the server system has an independent proprietary database that is configured with each lab's unique processing data. Since each lab uses different processing equipment (e.g. generators, blockers and edgers) they all must have their jobs calculated accordingly. The configuration database is maintained in coordination with requests from each lab. At installation time a service representative on-site that enters test jobs through the system to determine and fine tune the configuration database settings.

As can be seen in FIGS. 5 and 6, multiple client lab accounts correspond to geographically distributed optical labs. Each lab will be processing job requests and transmitting them via path 50*a* to its proprietary database within the server, for accessing the global resources. The invention applies the same technical and financial proprietary rules in a uniform manner to global software to generate unique technical and financial data that correspond to each individual patient's Rx.

Figure 7:
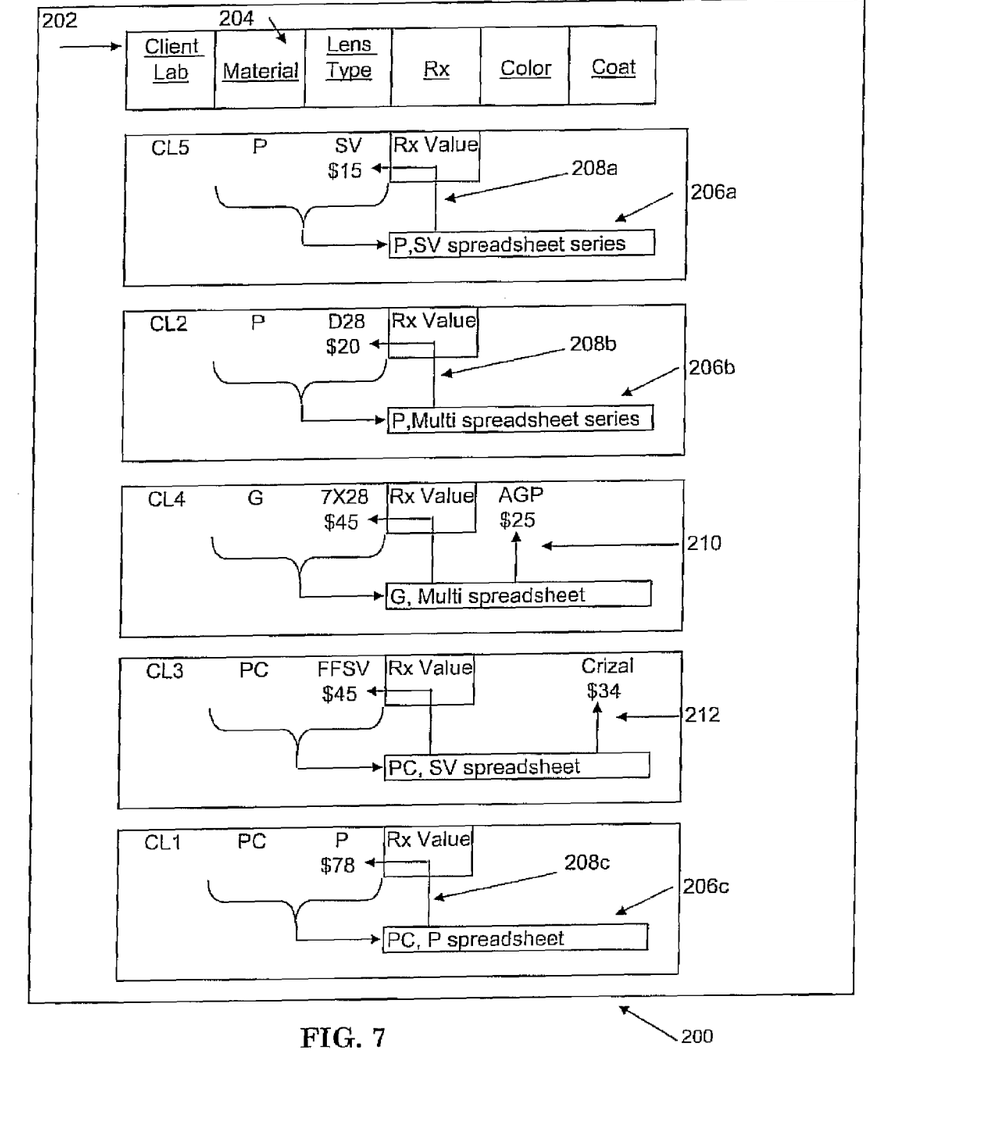
FIG. 7 is a schematic drawing showing sample invoices.

In FIG. 7 there is shown a sequence 200 of sample invoices. As the steps of processing job requests and running job requests are repeated, one portion of each completed job may consist of an invoice. The first column on the left 202 represents the client lab. Note the processed jobs are for random labs, e.g. CL5, CL2, CL4, CL3 and so on. Each job designates a material and a lens type. A non-exhaustive list of materials include plastic (P), glass (G), and polycarbonate (PC). Any existing or new material that is suitable for ophthalmic eyewear may be listed. A non-exhaustive list of lens types includes single vision, multi-focal and progressive, either grouped or individually. Other more specific lens features include bifocal with a 28 mm D-segment (D28), trifocal 7 times 28 mm (7×28), full field single vision (FFSV), and progressive (P). Other lens types are well known to those skilled in the art. Additional categories include the prescription (Rx) which might include sphere, power, lenticulars, over power, add power, add type, add size, prism, tints polarization, lens color, coating and compatible combinations thereof. Across all lens manufacturers, there are over 400,000 different lens SKU's (stock-keeping units). The client databases use these material, lens type, etc. categories to represent the group of lenses that are offered by that lab.

Material and lens type bracket 204 indicates that this combination is used to identify a particular financial spreadsheet series 206*a*, 206*b*, 206*c* from the respective client's proprietary data records. This is represented in FIG. 6 as price lists 126 and financial databases 128. From those spreadsheets, the server software can obtain the base price for the lens based on the prescription (Rx). This is shown by arrow 208*a*, 208*b* and 208*c*. The other spreadsheets in the series provide cost data for the various other lens features that the respective client lab offers. For CL4, a lens color know as autumn gold polarized (AGP) has been selected, resulting in an add-on charge 210. For CL3, a Crizal® brand coating has been selected, resulting in a different add-on charge 212. Accordingly, the labs use the same set of proprietary financial spreadsheets for all their jobs. However, each job can receive a unique invoice and price. So, each lab uses the same financial spreadsheets, e.g. it maintains the technical and financial data persistent across all of its jobs. The labs collective share the lens database and lens calculation software, as global resources. The system runs jobs randomly from the various labs as they are received and queued. The completed job with its unique machine interface files, and job ticket and invoice and accounting system extract file, is stored confidentially and transmitted back to the client lab.

Another embodiment of the system includes operating modes. For example, step 20 can be considered a calibrating mode. Machine settings are recorded and stored in the equipment configuration database 124. The is a one time set-up. The settings are not routinely changed, or updated though feedback assessing the machine's quality control or precision.

As a second example, step 40 can be considered the normal technical operating mode. Information is collected and transmitted to the server where it is processed with a combination of global and proprietary resources.

As a further example, step 60 can be considered a pricing/invoicing/AR mode. The price lists in database 126 and the financial information in database 128 can be uniformly applied to each job from the corresponding lab to provide unique pricing and printable invoice files for each patient's Rx. AR stands for accounts receivable, where an electronic extract file is provided which can be exported to each accounting software package specified by the labs. Each lab is charged a flat fee for each use of the lens calculation software. The labs may also be charged a flat monthly fee, or a fee based on the amount of storage space they occupy on the server, or the amount of CPU time they utilize on the server. Other payment plans involving a combination of these pricing methods may be employed.

Although illustrative embodiments of the present invention have been described herein, it is to be understood that the present invention is not limited to those precise embodiments, and that various other changes and modifications may be affected therein by one skilled in the art without departing from the scope or spirit of the present invention. All such changes and modifications are intended to be included within the scope of the invention as defined by the appended claims. For example, it is expressly intended that switched steps that result in substantially the same actions to achieve the same results are within the scope of the invention. Moreover, it should be recognized that any disclosed form or embodiment of the invention may be incorporated in any other disclosed or described or suggested form or as a general matter of compatibility of application method. It is the intention, therefore, to be limited only as indicated by the scope of the claims appended hereto.

What is claimed is:

1. A method of providing job invoicing information for customers of optical labs within a shared software pay-per-use environment, comprising the steps of:
   A) configuring an optical lab client computer for which an account is establish for each optical lab out of a plurality of optical lab client computer which all communicate with a lab management server over a geographically distributed telecommunications link, wherein each optical lab client account includes proprietary financial resources; wherein said configuring step includes (i) providing access to global technical resources comprising a global lens database and a lens surface grinding calculation program shared by all labs, and (ii) establishing proprietary data records for each optical lab client account by calibrating a lab's lens generating equipment and storing lens generating equipment parameters in an equipment configuration database;
   B) processing a job request for an individual prescription (Rx) via an order entry facility on the optical lab client computer and transmitting details of the job to the server;
   C) running the job request on the lab management serving utilizing global technical resources within a shared software pay-per-use environment including running the lens surface grinding calculation program with the lens generating equipment parameters of the requesting lab and returning completed job data including pricing, invoicing and electronic interface files for the lab's lens generating equipment to the optical lab client computer; and
   D) maintaining the same proprietary data records across multiple individual Rx orders including using the same lens generator equipment parameters with different electronic interface file for the respective lab's lens generating equipment.

2. The method of claim 1, wherein each of said plurality of optical lab client computers alternately submit new job requests, whereby the method further includes the steps of:
   repeating steps B) and C) for different optical lab client computer and for a sequence of unique lens orders, wherein each optical lab client computer uses its same proprietary lab parameters for all jobs.

3. The method of claim 1, wherein the global lens database includes data on more than 400,000 individual lens SKUs, and wherein the proprietary price lists categorize lenses by a combination of material and lens type, and wherein each category includes a series of financial spreadsheets based on another lens feature selected from the group consisting of sphere, power, lenticulars, prescription, over power, add power, add type, add size, prism, tints, polarization, lens colors, lens coatings and compatible combinations thereof.

4. The method of claim 1, wherein the lab's equipment includes a blocker and an edger.

5. The method of claim 4, wherein said configuring step includes calibrating the blocker, and the edger and storing equipment parameters in the equipment configuration database.

6. The method of claim 4, wherein the equipment configuration database is based on equipment type.

7. The method of claim 5, wherein the proprietary data records include price list and a financial database.

8. The method of claim 1, wherein said job processing step includes providing lens type and material data.

9. The method of claim 1, wherein said job processing step includes providing frame trace data.

10. The method of claim 1, wherein said job processing step includes scanning a lens package bar code.

11. The method of claim 1, wherein the returned completed job data includes a printable job ticket file.

12. The method of claim 1, wherein the returned completed job data includes a printable invoice file.

13. The method of claim 1, wherein the returned completed job data includes an extract file containing the invoice financials.

14. The method of claim 13, wherein the format of the extract file is determined by the proprietary data records.

15. The method of claim 14, wherein the format is suited for exporting the extract file to the particular labs accounting software.

16. A memory that stores instructions in a memory device of a client computer, or in a removable medium adapted to cooperate with at least one of a reader of the computer and a remote source via a telecommunications network, characterized in that the instructions are programmed for implementing the following step:
   A) configuring an optical lab client computer for which an account is established out of a plurality of optical lab client computers which all communicate with a lab management server over a geographically distributed telecommunications link, wherein each optical lab client account includes proprietary financial resources including price lists and a financial database, and wherein said configuring step includes (i) providing access to global technical resources comprising a global lens database and a lens surface grinding calculation program shared by all labs, and (ii) establishing proprietary data records for each optical lab client account by calibrating a lab's lens generating equipment and storing lens generating equipment parameters in an equipment configuration database;
   B) processing a job request for an individual prescription (Rx) via an order entry facility on the optical lab client computer and transmitting details of the job to the server;
   C) running the job request on the lab management server utilizing global technical resources within a shared pay-per-use environment including running the lens surface grinding calculation program with the lens generating equipment parameters of the requesting lab and returning completed job data including pricing, invoicing and electronic interface files for the lab's lens generating equipment to the optical lab client computer; and
   D) maintaining the same proprietary data records across multiple individual Rx orders including using the same lens generating equipment parameters with different electronic interface files for the respective lab's lens generating equipment.

17. A memory that stores instructions in a memory device of a server computer, or in a removable memory medium adapted to cooperate with at least one of a reader of the computer and a remote source via a telecommunications network, characterized in that the instructions are programmed for implementing the following steps:
- A) configuring an optical lab client computer for which an account is established out of a plurality of optical lab client computers which all communicate with a lab management server over a geographically distributed telecommunications link, wherein each optical lab client account includes proprietary financial resources including price lists and a financial database, and wherein said configuring step includes (i) providing access to global technical resources comprising a global lens database and a lens surface grinding calculation program shared by all labs, and (ii) establishing proprietary data records for each optical lab client account by calibrating a lab's lens generating equipment and storing lens generating equipment parameters in an equipment configuration;
- B) processing a job request for an individual prescription (Rx) via an order entry facility on the optical lab client computer and transmitting details of the job to the server;
- C) running the job request on the lab management server utilizing global technical resources within a shared pay-per-use environment including running the lens surface grinding calculation program with the lens generating equipment parameters of the requesting lab and returning completed job data including pricing, invoicing, and electronic interface files for the lab's lens generating equipment to the optical lab client computer; and
- D) maintaining the same proprietary data records across multiple individual Rx orders including using the same lens generating equipment parameters with different electronic interface files for the respective lab's lens generating equipment.

18. A system for processing a plurality of unique ophthalmic lens job requests including invoicing information for patients of optical labs within a shared software pay-per-use environment, comprising:
- an optical lab client computer for which an account is established out of a plurality of optical lab client computers; the optical lab client computer having an order entry facility for collecting individual lens data including prescription data and for initiating a job request to a lab management server;
- a telecommunications link for operatively connecting said plurality of optical lab client computers to the lab management server;
- a lab management server having (i) global services including a lens database to identify one of lens properties and lens type from the job request, (ii) proprietary technical and financial data records for each client lab, and (iii) global lens surface grinding calculation software that is customized for each lab by the proprietary data; and
- lens generating equipment having machine parameters and calibrations that are stored within an equipment configuration database within the proprietary technical data records for interacting with the global lens surface grinding calculation software within a share pay-per-use environment to provide unique lens calculations to be generated according to a corresponding job ticket, wherein the lens calculations include pricing, invoicing, and electronic interface files for the lens generating equipment that are transmitted to the optical lab client computer;
- wherein the proprietary data allows a plurality of client labs to share global resources including using the same lens generator equipment parameters and calibrations with different electronic interface files to deliver a continuous series of individual lenses for the respective lab's generating equipment and provide corresponding individual pricing for electronic and paper invoicing.

19. The system of claim 18, comprising three operating states including: a calibration mode for recording settings of said generating equipment within the proprietary technical data records; a normal operating mode where unique lens jobs are sequentially processed; and a financial mode for delivering individual pricing and individual invoicing and individual accounts receivable electronic extract files to the lab.

20. The system of claim 19, wherein the system initially operates in calibration mode to set up a new lab as an additional client account on the server.

21. The system of claim 20, wherein after the initial operation of the calibration mode, the system interacts with existing client accounts to alternately operate between normal operating mode and financial mode to produce a continuous stream of unique job tickets, lenses, invoices, and accounting extract files all corresponding to a particular Rx.

22. The system of claim 21, once the system exits calibration mode, the generating equipment is isolated from providing quality control feedback to the server.

23. The system of claim 22, wherein operation within the calibration mode comprises recording equipment settings for a blocker and edger, wherein the equipment settings are based on equipment type and equipment calibration.

24. The system of claim 18, wherein said order entry facility collects additional lens data selected from the group consisting of lens type, lens material, frame trace data, scanned lens package bar code data, and combinations thereof.

25. A software product adapted to be stored in a memory of a client computer, or in a removable medium adapted to cooperate with at least one of a reader of the computer and a remote source via a telecommunications network, characterized in that it includes instructions for interacting with at least one element of the system according to claim 18.

26. A software product including lab management software adapted to be stored in a memory of a server computer, or in a removable medium adapted to cooperate with at least one of a reader of the server computer and a remote source via a telecommunications network, characterized in that it includes instructions for interacting with at least one element of the system according to claim 18.

* * * * *

UNITED STATES PATENT AND TRADEMARK OFFICE
CERTIFICATE OF CORRECTION

PATENT NO. : 8,333,469 B2
APPLICATION NO. : 12/112518
DATED : December 18, 2012
INVENTOR(S) : Mike Filipovich et al.

Page 1 of 1

It is certified that error appears in the above-identified patent and that said Letters Patent is hereby corrected as shown below:

On the Title Page, item (73), line 3, delete "le" and insert --Le--;

In the Claims

Column 9, line 20 (claim 1, line 6), delete "computer" and insert --computers--;

Column 9, line 36 (claim 1, line 22), delete "serving" and insert --server--;

Column 9, line 54 (claim 2, line 5), delete "computer" and insert --computers--;

Column 10, line 8 (claim 7, line 2), delete "list" and insert --lists--;

Column 10, line 32 (claim 16, line 6), delete "step" and insert --steps--; and

Column 12, line 2 (claim 18, line 24), delete "share" and insert --shared--.

Signed and Sealed this
Thirtieth Day of April, 2013

Teresa Stanek Rea
*Acting Director of the United States Patent and Trademark Office*

UNITED STATES PATENT AND TRADEMARK OFFICE
CERTIFICATE OF CORRECTION

PATENT NO. : 8,333,469 B2  
APPLICATION NO. : 12/112518  
DATED : December 18, 2012  
INVENTOR(S) : Mike Filipovich et al.

Page 1 of 1

It is certified that error appears in the above-identified patent and that said Letters Patent is hereby corrected as shown below:

On the Title page, item (73), lines 4 and 5, insert --Optifacts, Inc.
Dallas, TX 75234 (US)--.

Signed and Sealed this
Twenty-fourth Day of September, 2013

Teresa Stanek Rea
*Deputy Director of the United States Patent and Trademark Office*